United States Patent
Zink (10) Patent No.: US 11,067,651 B2
(45) Date of Patent: Jul. 20, 2021

(54) LOCAL KNEE COIL FOR A MAGNETIC RESONANCE IMAGING DEVICE

(71) Applicant: Siemens Healthcare GmbH, Erlangen (DE)

(72) Inventor: Stephan Zink, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 338 days.

(21) Appl. No.: 16/170,447

(22) Filed: Oct. 25, 2018

(65) Prior Publication Data

US 2019/0128978 A1 May 2, 2019

(30) Foreign Application Priority Data

Oct. 27, 2017 (EP) .................................. 17198790

(51) Int. Cl.
*G01R 33/34* (2006.01)
*G01R 33/30* (2006.01)
*A61B 5/055* (2006.01)

(52) U.S. Cl.
CPC ........ *G01R 33/34084* (2013.01); *A61B 5/055* (2013.01); *G01R 33/30* (2013.01); *G01R 33/34007* (2013.01)

(58) Field of Classification Search
None
See application file for complete search history.

(56) References Cited

U.S. PATENT DOCUMENTS 5,066,915 A 11/1991 Omori et al.
9,250,302 B2 2/2016 Driemel et al.
(Continued)

FOREIGN PATENT DOCUMENTS

CN 102313875 A 1/2012
CN 106872918 A 6/2017
(Continued)

OTHER PUBLICATIONS

European Office Action for European Patent Application No. 17 198 790.2-1115, dated Apr. 18, 2019.
(Continued)

*Primary Examiner* — Katherine L Fernandez
(74) *Attorney, Agent, or Firm* — Lempia Summerfield Katz LLC (57) ABSTRACT

A local knee coil is provided for a patient table of a magnetic resonance imaging device. The local knee coil includes a connecting device, a feet support element, and a coil unit. The coil unit includes coil elements. The connecting device is configured for connecting to a socket in the patient table. The connecting device includes at least one interface unit for multiple channels corresponding to the coil elements. The connecting device includes at least one guiding element to fit the connecting device into the socket that is displaced from the knee position on the patient table and functions as a receptacle for the connecting device to form a positive connection and interconnect the interface units during the fit. The feet support element is configured for the feet of a patient whose knee extends through the coil unit in the knee position, that is positioned on the top of the connecting device.

10 Claims, 7 Drawing Sheets

(56) References Cited

U.S. PATENT DOCUMENTS

| | | | |
|---|---|---|---|
| 2007/0016003 A1* | 1/2007 | Piron | A61B 90/11 |
| | | | 600/415 |
| 2010/0315085 A1* | 12/2010 | Brown | G01R 33/34084 |
| | | | 324/309 |
| 2011/0030698 A1 | 2/2011 | Kaufman | |
| 2011/0279119 A1 | 11/2011 | Driemel | |
| 2013/0023756 A1* | 1/2013 | Driemel | G01R 33/28 |
| | | | 600/422 |
| 2013/0097780 A1* | 4/2013 | Biber | A61B 5/0555 |
| | | | 5/601 |
| 2013/0184563 A1 | 7/2013 | Driemel | |
| 2014/0039301 A1 | 2/2014 | Driemel | |
| 2015/0355296 A1 | 12/2015 | Harder | |
| 2017/0168126 A1* | 6/2017 | Jeong | G01R 33/341 |
| 2018/0252782 A1 | 9/2018 | You | |

FOREIGN PATENT DOCUMENTS

| | | |
|---|---|---|
| CN | 207837547 U | 9/2018 |
| DE | 102011079565 A1 | 1/2013 |
| DE | 102012213594 A1 | 2/2014 |

OTHER PUBLICATIONS

European Search Report for European Patent Application No. 17198790.2-1115 dated Mar. 23, 2018.
Chinese Office Action for Chinese Application No. 201811253870.4 dated Aug. 17, 2020, with English translation.

* cited by examiner

LOCAL KNEE COIL FOR A MAGNETIC RESONANCE IMAGING DEVICE

CROSS REFERENCE TO RELATED APPLICATIONS

This patent application claims priority from European Patent Application no. 17198790.2 filed on Oct. 27, 2017, which is hereby incorporated in its entirety.

FIELD

Embodiments relate to a local knee coil for a patient table of a magnetic resonance imaging device.

BACKGROUND

Magnetic resonance imaging is an established technique in medical areas, for example for diagnosis. Images with a high signal to noise ratio (SNR) may be acquired using so-called local coils. Local coils are antenna systems placed in close proximity to the patient, for example on the patient (anterior placement) or under the patient (posterior placement). Local coils may include a plurality of coil elements, e.g. single antennas. During a magnetic resonance measurement, the excited nuclei induce voltages into the coil elements, that, as magnetic resonance signals, may, for example, be amplified using a low noise amplifier (LNA preamp) and may be transported via a cable to a receiving system of the magnetic resonance imaging device.

The SNR may be further improved by using high field systems, for example that include a basic magnetic field strength of 1.5 T to 12 T and more.

Each receiving coil element may define a receiving channel. The number of coil elements used in a magnetic resonance imaging device may be larger than the number of channels of a receiving system, so that a switch matrix may be used to route the currently active receiving channels (positioned in the field of view/homogeneity volume of the magnetic resonance imaging device) to the existing receivers. Thus, more coil elements than receivers may be used, since when the whole body of the patient is covered by coil elements, only the coil elements inside the field of view or inside the homogeneity volume, respectively, have to be read out.

A local coil is an antenna system including one or more coil elements and may also be called a coil array. The single coil elements may be provided as loop antennas, butterfly coils and/or saddle coils. In addition to the coil elements, a local coil may include a pre-amplifier (LNA), further electronic components, for example baluns, cables, a housing, and a connection assembly including a plug and cable to connect the local coil to the magnetic resonance imaging system, for example using corresponding sockets of a patient table. The receivers of the receiving system of the magnetic resonance imaging device may filter and digitize a magnetic resonance signal received by the coil elements of the local coil and transfer the data to a digital signal processing system, so that an image and/or a spectrum may be derived from the magnetic resonance data. Images and spectra may be displayed to a user for diagnosis.

Dedicated local coils have been proposed for imaging the lower extremities of a patient, for example the knees and the feet of the patient. To fulfil certain requirements of orthopaedic imaging, the local coils may be configured as transmitting as well as receiving coils. That is, not or not only the body coil enclosing the whole body is used to excite the atomic nuclei, but also or only the local coil, that only covers parts of the body. The same local coil is then also used to receive magnetic resonance signals. Two different concepts have been proposed. In a first concept, a transmitting coil element is also the receiving coil element, in a second concept, the transmitting coil elements and the receiving coil elements are electrically isolated and separated from each other, but mechanically provided in the same housing. This second concept allows receiving multiple channels simultaneously, accelerating the imaging process by using parallel imaging techniques and obtaining higher signal to noise ratio (SNR).

The antennas of the second concept have the disadvantage that the mechanical design of the coil has to be chosen such that as many patients as possible fit into the local coil while including the local coil as proximate as possible to the patient. Usually, the local coils are configured to accommodate 80 to 98% of the patients. However, for patients with larger extremities or patients wearing a bandage and/or having ankylosis, the narrow dimensioning of the housing of the local coil may not allow any movement or even placing the corresponding extremity inside the local coil. For many orthopaedic questions, however, imaging in different positions and/or real time imaging at, for example, 0.25 to 30 frames per second are of high significance. It is, for example, known to image a knee of a patient in different angular positions and/or image foot joints twisted and/or under load. The functional imaging is very important in orthopaedic diagnosis. The electric and mechanical design of known local coils, however, hinders or even prevents application.

Additionally, the contacting of the local coil has potential for improvement. Direct connect coils have been proposed as local head coils and/or local spine coils. Direct connect coils include a base including at least one guiding element to slidingly fit the base and thus the whole local head or spine coil into a corresponding direct connect circuit, such that the electrical connections to and from the coil elements are established. In this manner, no cables are required, since these local head or spine coils are immediately positioned in a suitable place on the patient table. Such a direct connect local head coil is, for example, known from DE 10 2011 079 565 A1, while U.S. Pat. No. 9,250,302 B2 discloses an adaptor for a direct-connection head coil with adjustable tilt angle.

However, direct connect sockets are only provided in the head area of a patient table, such that all remaining known local coils require cables, that, according to the type of local coil, may have different thicknesses, for example of 20 mm for pure receiving local coils, or 12 mm for receiving and transmitting local coils. The presence of the cable is disadvantageous when positioning patients on the patient table, since the cables may be damaged or get jammed. Also, safety issues ensue, since, for example, baluns inside the cables may malfunction, possibly leading to burns of the patient.

Another problem specific for knee coils is that the patient's knee is positioned while the patient is sitting. As soon as the patient lies down to a horizontal position, the knee joint is displaced in the direction of the head of the patient. The displacement effect should be considered.

The cable may be kept as short as possible, for example to reduce the danger of jamming, but also to increase the convenience of the patient. If the cable from the local coil to the next socket is as short as possible, the risk of an uncomfortable position of the patient on the cable, jamming of the cable and burns due to malfunctioning electronic components is reduced. Cushions including defined recesses may be used to guide the cable and allow the patient to comfortably lie on the cushion. Furthermore, tube holders using guide rails or guide grooves of the patient table have been proposed. Local coils may be provided with exchangeable cables, that may be chosen in a length as short as possible and as required.

In Chinese utility model application 201720201724.1, a local extremity coil has been proposed, in which the cable or the electrical connections, respectively, are guided partly in the housing of the local coil. In this manner, the fraction of the cable running on top of the patient table may be reduced. Due to transmitting functions of the local coils, a certain socket of the patient table is chosen, leading to problems when imaging the right knee. If the right knee is positioned inside the local coil, the left leg has to be guided around the local coil and has to be positioned on top of this socket and the corresponding plug. Thus, the plug has to be cushioned and is subject to damage.

Regarding the displacement effect when the patient moves from a sitting position to a lying position, the knee may be positioned off-centre, displaced by an estimated movement distance. This estimation, however, performed by medical personal, is error-prone and may result in reduced quality of the magnetic resonance data.

SUMMARY AND DESCRIPTION

The scope of the present disclosure is defined solely by the appended claims and is not affected to any degree by the statements within this summary. The present embodiments may obviate one or more of the drawbacks or limitations in the related art.

Embodiments provide a local knee coil with increased comfort for the patient and with reducing the risk of damage and/or burns to the patient.

A local knee coil for a patient table of a magnetic resonance imaging device includes a connecting device for connecting to a socket in the patient table, the connecting device including at least one interface unit for multiple channels corresponding to coil elements of the local knee coil and connecting to a corresponding interface unit of the socket, and a coil unit including the coil elements for sending excitation signals and/or receiving magnetic resonance signals. The connecting device includes at least one guiding element to slidingly fit the connecting device into the socket that is displaced from the knee position on the patient table and functions as a receptacle for the connecting device, to form a positive connection and interconnect the interface units during the slide-fit. The local knee coil further includes a feet support element for the feet of a patient whose knee extends through the coil unit in the knee position. The feet support element is positioned or positionable on the top of the connecting element.

Thus, the socket used is a direct connect socket, for example, a direct connect socket for a local head coil. An extended plug is used, e.g. the connecting device, that fits into a direct connect socket of the patient table, e.g. uses guiding elements corresponding with guiding elements of the direct connect socket to slidingly fit the connecting device into the socket and at the same time establishing the electrical connections via the interface units. Additionally, the connecting device serves as a feet support element or provides a space for a feed support element. For example, the feet support element may include a top portion of the connecting device, for example by providing the top of the connecting device with a cushion gutting out over the surface of the patient table.

The local knee coil is electrically connected using the direct connect socket of the patient table used for direct connect head coils. The connection provides for minimal use of cables or even a construction in which no cables are needed, as discussed below. If the local knee coil is ab cable, the cable may be guided along lateral areas, preventing discomfort for the patient. The installation of the coil on the patient table is also facilitated since a direct connect socket is used, providing mechanical fit and electrical connection in one single action. The connecting device itself poses no obstacle in positioning the patient like known plugs do, since the connecting device is at least largely received in the direct connect socket and additionally provides the feed support unit even assisting in a comfortable positioning of a patient.

In an embodiment, that the connecting device and the coil unit are connected by a cable, so that the coil unit may be freely positioned, for example, at the knee position, while the cable is placed in lateral areas without contact to the legs or feet of the patient. The local knee coil does not include a plug but is connected using the direct connect socket in the patient table by the connecting device. Cables are still present, but neither the cables nor the plug interfere with the positioning of the feet and lower legs of the patient. The connecting device may include recesses or the like for the feet/legs and/or at least parts of the feet supporting element, for example a cushion.

However, in an embodiment, the local knee coil is a modified direct connect coil without any cable visible or present on the outside of the local knee coil.

The local knee coil includes a displacement device for displacing at least a part of the coil unit to the knee position on the patient table when the connecting device is connected in the socket. The displacement device may thus mechanically couple the coil unit and the connecting device to each other so that the coil unit may be displaced manually from the position of the direct connect socket to the corresponding knee position on the patient table, for example, using degrees of freedom provided by the displacement device. In this manner, the local knee coil construction is compact and provides easy handling by medical staff.

In an embodiment, the displacement device includes at least one guide element engaging a guide element of the coil unit to slidably move the coil unit into the knee position. For example, the sliding movement of the coil unit follows a longitudinal direction of the patient table when installed. The displacement device includes guides, for example, at least one guide rail. The connecting element is slid into the direct connect socket such that mechanical and electrical connection is provided. The coil unit, appropriately guided, may then be displaced/pulled out, for example, in the longitudinal direction of the patient table, to the knee position. In this manner, an area on top of the connecting device is exposed, that may be used for supporting the feet of the patient, for example, using cushions and/or recesses according to the anatomy. No cables and no plugs interfere with the positioning of the patient.

The coil unit may be provided including an assembly including the coil elements and a guide frame supporting the assembly. The guide frame includes at least one handle for manually sliding the coil unit. Such a handle may also be used for transporting the local knee coil, comparable to a suitcase, when the coil unit is in its base position on top of the connecting device.

To establish electrical contact between the coil elements and the interface unit of the connecting device, in a first option, the guide elements may include a sliding contact for electrically connecting the coil elements to the interface unit of the connecting device. The sliding contact does not have to span the whole length of possible displacement, since the presence of an electrical connection suffices in displacement positions in which the coil unit is to be used to acquire magnetic resonance signals.

In a configuration, that provides permanent electrical connection, the local knee coil may include a cable guiding device, for example, a dragchain device, for internally guiding a cable (or wires, respectively) connecting the coil elements to the interface unit of the connecting device. Such a cable guiding device may include one or more guide pulleys for the cable. For example, a guide pulley may be fixed against a restoring force of a spring element in the coil unit or the connecting device, such that the cable is taut in each position of the coil unit relative to the connecting device.

The guide elements of the displacement device may include a guide rail and corresponding protrusions engaging the guide rail, for example sword-shaped and/or U-shaped protrusions.

The local knee coil may further include a latching and/or snapping device to secure the coil unit to the connecting device when the coil unit is in its end position atop the connecting device (base position). The guide elements of the displacement device may include an end stopper defining an end position in which the coil unit is maximally displaced from the connecting device.

The coil unit may not be fully displaced into the end position, but at a distance of, for example, 2-5 cm from the end position. In this manner, when the patient, after placement of the knee inside the coil unit, lies down from a sitting position, the coil unit follows the ensuing movement of the knee in the direction of the head of the patient, maintaining the relative position of the coil elements and the knee. Using a displacement device with guide elements allowing sliding displacement of the coil unit of the local knee coil to the knee position on the patient table, the retraction effect when the patient lies down may be compensated, so that off-centre positioning of the knee in an estimated position may be omitted.

In an embodiment, the guide elements of the displacement device include at least one intermediate stopper displaced from an end stopper defining a maximum displacement of the coil unit and/or an intermediate mechanical resistance element displaced from the end stopper defining a maximum displacement of the coil unit. The displacement of the intermediate stopper/resistance element from the end stopper of maximum displacement from the connecting device is between 2 and 5 cm, for example 3 cm. Ideal intermediate displacements of the coil unit for positioning the knee while the patient is still sitting are communicated to the medical staff and sufficient compensating length to compensate a movement of the knee when the patient lies down is retained. If the knee moves while the patient is lying down, the coil unit, guided by the displacement device, moves accordingly such that a centre position of the knee in the coil unit is maintained.

The local knee coil of this embodiment may further include a way sensor for measuring displacement of the coil unit relative to the connecting device, for example when the patient is lying down from a sitting position after the knee was positioned inside the coil unit. The displacement data may be communicated to a control device of the magnetic resonance imaging device, for example, using a connector of the interface units, and may, for example, be used for auto-positioning functions and the like. The position of the centre of the coil unit and/or the coil elements is thus always known to the control device.

In an embodiment of the local knee coil, the displacement device includes a hinge connecting at least part of the coil unit to the connecting device. The at least part of the coil may be swung out from atop the connecting device to the knee position. The local knee coil is therefore hinged or foldable. The connecting element, functioning as a base, slides into the direct connect socket of the patient table, providing mechanical and electrical connection in one action. The coil unit or at least part of the coil unit, that may include a hinging frame in addition to an assembly including the coil elements, may be swung into the knee position. Additional coil unit parts may be added. The hinging frame, for example, also connecting hinges on both lateral sides of the local knee coil, may include at least one handle facilitating the swinging of the coil into the knee position and the transportation of the local knee coil when folded up.

The coil unit is split into an upper coil unit part and a lower coil unit part, the hinge connecting the lower coil unit part and the connecting device such that the lower coil unit part may be swung out from atop the connecting device to the knee position. The upper coil unit part may be set atop the lower coil unit part using a connection when the lower coil unit part is swung out. In use, the connecting device is first fittingly slid into a direct connect socket on the patient table, whereafter the lower coil unit part is swung out to the knee position and the upper coil unit part is added, for example by locking it in place by a snap-in locking device as the connection.

The connecting device may include a recess for the lower coil unit part. The feet support element is positionable in the recess when the lower coil unit part is swung out. The lower coil unit part may be at least almost completely accommodated in the recess when swung in. Folded up, the lower coil unit part at least partly "vanishes" inside the recess of the connecting device. If the lower coil unit part is swung out of the recess, the recess is used as a support for the feet support element, for example a cushion.

An attachment, for example a hook, are provided to attach the upper coil unit part to the lower coil unit part and/or the connecting device when the lower coil unit part and the connecting device are in hinged position (folded up). As explained above, the lower coil unit part may be retracted into the recess in this hinged position. The upper coil unit part may be attached to the assembly of the connecting device and the lower coil unit part for transportation. If the local knee coil is to be used for a magnetic resonance measurement, the upper coil unit part is removed from this assembly, the connecting device is slid into the direct connect socket and the lower coil unit part is swung out. The patient may be positioned, and the coil unit may be closed by adding the upper coil unit part. After this, the imaging may commence.

The electrical connection between the coil elements and the interface unit may be guided through the at least one hinge.

An assembly including the coil elements may be supported by a frame, for example, a guide frame or a hinging frame, that includes at least one handle for manually displacing the coil unit and/or transporting the local knee coil. Using the handle, the local knee coil may be easily transported with one hand. With the coil unit in its base position and, if applicable, the upper coil unit part attached, the local knee coil is compact and easy to carry using the handle. Due to the compact design of the local knee coil, it is also easily stowed away.

The provision of a frame also provides the realisation of an adjustment device for fine-adjusting the assembly including the coil elements carried by the frame. For example, such an adjustment device may allow lateral movement of the assembly relative to the guide frame for fine-positioning of the assembly and thus the coil elements to accommodate the patient as comfortable as possible.

In an embodiment, the local coil unit includes at least one guiding protrusion and/or guiding recess interoperable with a corresponding guiding recess and/or guiding protrusion of the patient table. Often, patient tables of magnetic resonance imaging devices include guiding recesses, that may also be used by the coil unit to aid in positioning the coil unit at the knee position, for example when the displacement device provides a certain clearance and/or backlash.

The feet support element may include at least one cushion and/or at least one anatomy recess element shaped for receiving a part of the anatomy of the patient. In this manner, a comfortable positioning of the patient is achieved.

Embodiments provide a magnetic resonance imaging device, including a patient table with a direct connect socket, for example for a head coil, and a local knee coil configured for connecting to the direct connect socket.

The interface unit of the direct connect socket may include connectors for sending excitation signals and receiving magnetic resonance signals. In this manner, the local knee coil and its coil elements may be used for transmitting as well for receiving (TX and RX). In an embodiment, if the interface unit of the direct connect socket only includes connectors for receiving magnetic resonance signals, the magnetic resonance imaging device may include an inductive coupling device for communicating excitation signals to the local knee coil.

DETAILED DESCRIPTION

Figure 1:
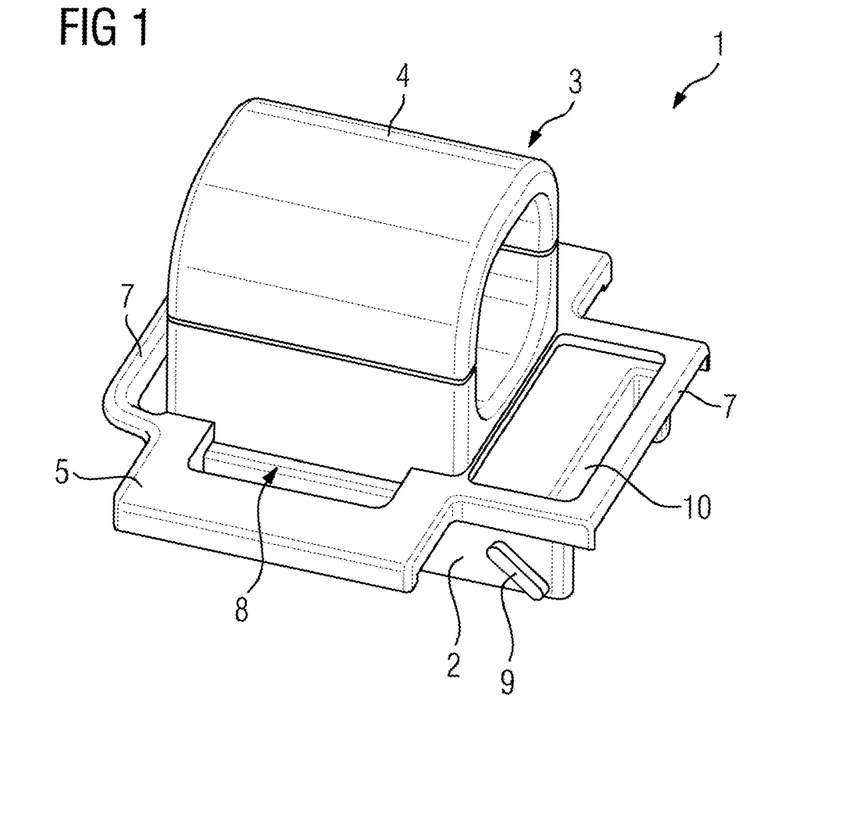
FIG. 1 depicts a perspective view of an embodiment of a local knee coil.
Figure 2:
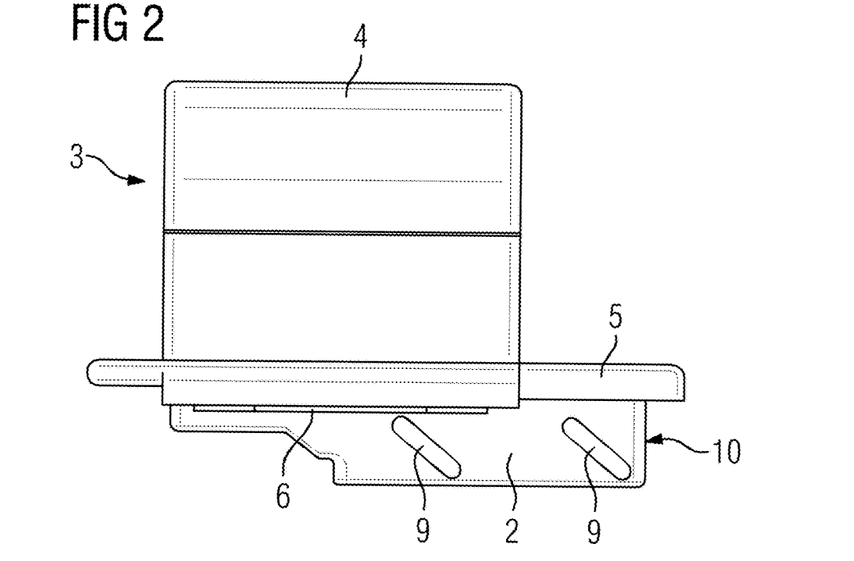
FIG. 2 depicts a side view of the local knee coil of FIG. 1.

FIG. 1 depicts an embodiment of a local knee coil 1 in a perspective view. FIG. 2 depicts a side view.

The local knee coil 1 includes a connecting device 2 and a coil unit 3, the coil unit 3 including an assembly 4 for the coil elements (not shown) of the local knee coil 1 and a guide frame 5 carrying the assembly 4. The coil unit 3 is connected to the connecting device 2 by a displacement device 6 only indicated in FIG. 2. The displacement device 6 includes a guide, for example guide elements, to provide sliding displacement of the coil unit 3 relative to the connecting device 2 along the longitudinal direction of a patient table, that is the left-right-direction of FIG. 2. The displacement device 6 is further described below with respect to FIG. 3.

The guide frame 5 includes at least one handle 7 that facilitates transportation of the local knee coil 1 when the coil unit 3 is in its base position (the end position atop the connecting device 2) as well as the displacement of the coil 3 relative to the connecting device 2. Additionally, an adjustment device providing lateral movement of the assembly 4 may be provided, as indicated by the lateral clearances 8 visible in FIG. 1. Handles 7 may be provided on both longitudinal sides of the frame 5.

The connecting device 2 is configured to slide-fit into a direct connect socket of a patient table, as described further below. To facilitate this sliding-fit into a positive mechanical connection and electrical connection of interface units in one action, guiding elements 9, in this case sword-shaped, are provided at the sides of the connecting device 2. The interface unit 10 is only indicated in the figures and includes connectors at least for each of the coil elements. The corresponding direct connect socket also supplies data for transmitting excitation signals by the coil elements. In such a case, the connecting device 2, that may also be referred to as a base of the local knee coil 1, may also house electronic/electrical components related to the transmitting functionality (TX) of the local knee coil 1.

Alternatively, TX data may also be communicated by induction, so that the local knee coil 1 (as well as the further embodiments) may also include an inductive coupling device for TX.

Figure 3:
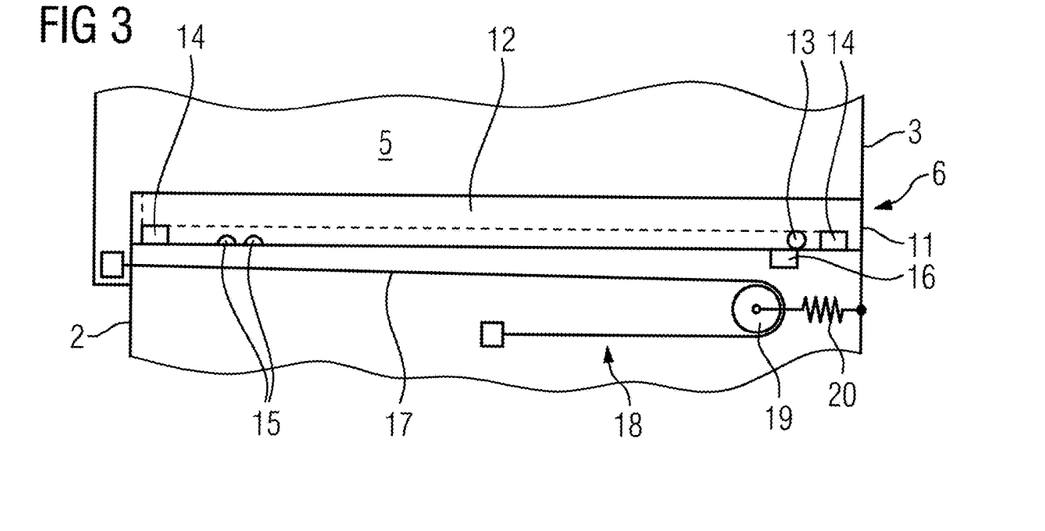
FIG. 3 depicts a detail of the displacement device and electrical connections according to an embodiment.

FIG. 3 depicts an embodiment of the displacement device 6 used in the first embodiment of the knee coil 1. The coil unit 3 and the connecting device 2 are schematically shown. The connecting device 2 includes a guide rail 11 as a guide element of the displacement device 6. The guide element 12 of the frame 5 runs in the guide rail 11 and may, for example, include a protrusion and/or even one or more wheels 13 running in the guide rail 11. The guide rail 11 includes two end stoppers 14 defining respective end positions of the coil unit 3, for example, the base position atop the connecting device 2 and the maximally displaced end position. Associated with at least one of the end stoppers 14 or as part of the respective end stoppers 14 a latching and/or snapping device may be provided to secure the coil unit 3 to the connecting device 2 when the coil unit 3 is in a corresponding end position. Such a latching and/or snapping device is not shown in FIG. 3 yet may be provided at least for the base position to facilitate transportation. Manual operating elements may be provided to unlock the latch- or snap fit. In other embodiments, the displacement device 6 may also include braking and/or locking devices to lock the coil unit 3 in an intermediate position.

In this preferred embodiment, however, the guide rail 11 includes an intermediate mechanical resistance element 15 that is provided at a distance of three cm away from the end stopper 14 of the maximally displaced position of the coil unit 3 relative to the connecting device 2. In this manner, haptic feedback is provided regarding this intermediate position. The displacement of the coil unit 3 may be stopped at the intermediate position defined by the resistance elements 15 and the knee of the patient may be positioned in the centre of the coil unit 3 while the patient is sitting. If the patient lies down to a horizontal position from the sitting position after the knee has been positioned with respect to the coil elements of the coil unit 3, the knee will be further displaced in the direction of the head of the patient, pulling the coil unit 3 over the correspondingly designed resistance element 15 closer to the end stopper 14 such that the relative position of the knee in the coil unit 3 does not change and the movement of the knee is compensated.

The local knee coil may further include a way sensor 16, also shown in FIG. 3, that measures the displacement of the coil unit 3 relative to the connecting device 2, that is in a defined position once slidingly fitted into the direct connect socket of the patient table. The data of the way sensor 16 is communicated to a control device of the magnetic resonance imaging device to provide functions like, for example, auto-positioning.

FIG. 3 further depicts a possible embodiment of an electrical connection across the displacement device 6. In this case, corresponding connection wires 17 are guided using a dragchain device 18 including a pulley 19 supported against the restoring force of a spring 20. Alternatively, a sliding contact at least along a length proximal to the end stopper 14 of the maximally displaced end position may be used.

Figure 4:
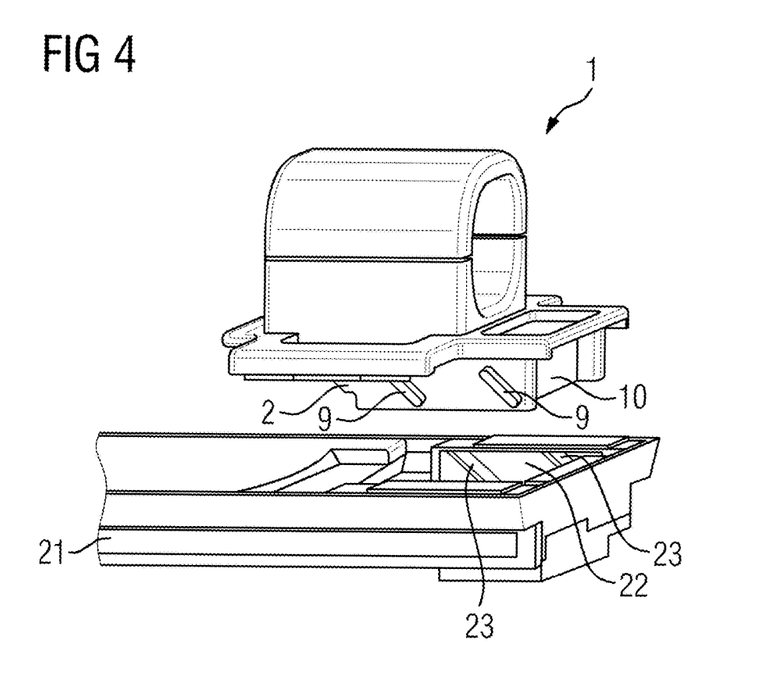
FIG. 4 depicts using the local knee coil according to an embodiment.

FIG. 4 illustrates usage of the local knee coil 1. A patient table 21 of a magnetic resonance imaging device includes a direct connect socket 22 at a position such that a direct connect local head coil may be connected electrically and mechanically in one action. The socket 22 includes guiding elements 23 corresponding to the guiding elements 9 of the connecting device 2. By cooperation of the guide elements 9, 23, the connecting device 2 is slidingly fit into the direct connect socket 22, thereby also connecting the interface unit 10 to a corresponding interface unit of the direct connect socket 22.

Figure 5:
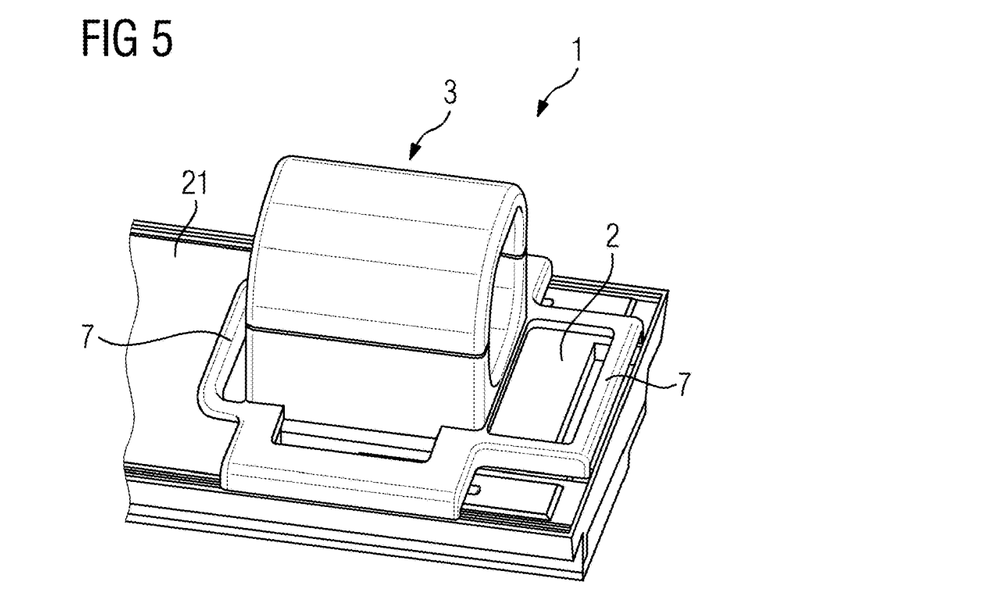
FIG. 5 depicts the local knee coil according to an embodiment installed on a patient table.

FIG. 5 depicts the local knee coil 1 installed on the patient table 21, where the coil unit 3 is still in its base position. Using, for example, one of the handles 7, the coil unit 3 may be slidingly displaced from the connecting device 2 that remains fixed, e.g. positively connected, in the direct connect socket 22.

Figure 6:
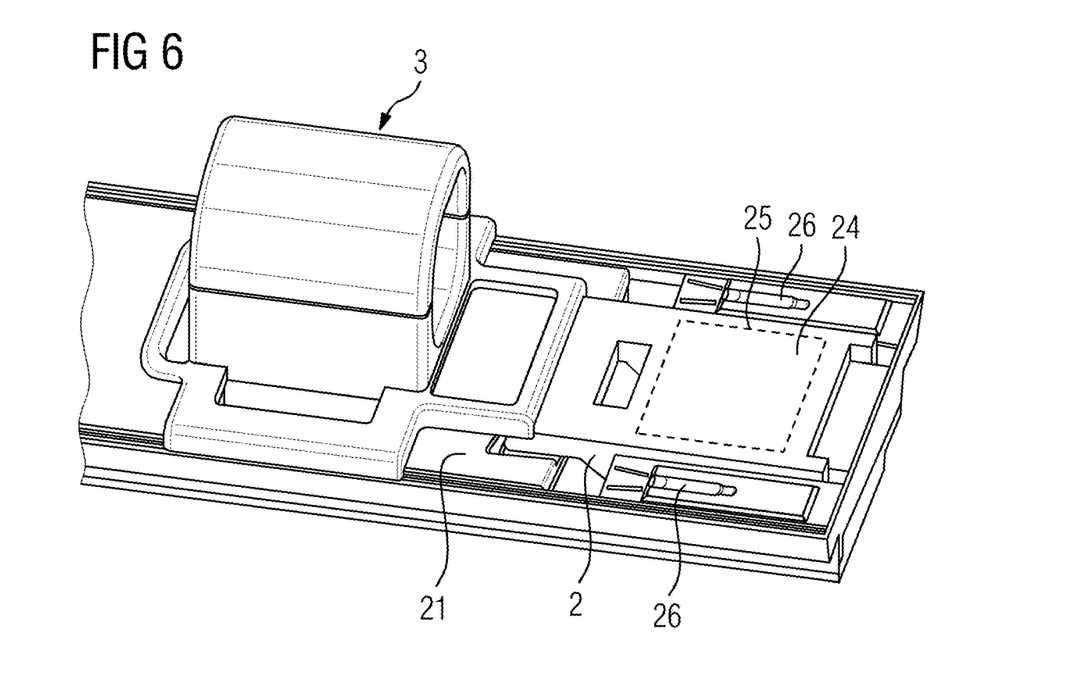
FIG. 6 depicts using a local knee coil according to an embodiment.

FIG. 6 depicts the coil unit 3 in its maximally displaced position, e.g. the knee position, on the patient table 21. The top 24 of the connecting device 2 is exposed forming a flat feet support element for the feet of the patient. However, the top 24 of the connecting device 2 may also include a recess for a feet support element 25 and/or a comfort element as feet support element 25, for example, a cushion. Finally, it is also possible to use anatomy recess elements shaped for receiving a part of the anatomy of the patient, for example the feet or lower legs, as feet support element 25, that may be provided as part of the top 24 or placed in corresponding recesses atop the connecting device 2.

The further sockets 26 of the patient table 21 do not have to be used, such that no plugs and/or cables hinder positioning of the patient.

FIGS. 7 to 11 depict an embodiment of a local knee coil 1'. Corresponding components are marked with the same reference numerals.

The second embodiment differs from the first embodiment in the configuration of the displacement device 6, that includes two lateral hinges 27 so that a hinging frame 28 of the coil unit 3 may be swung out from a position atop the connecting device 2 to the knee position on the patient table 21. The hinging frame 28 includes two lateral handles 7.

As depicted in FIG. 7 to FIG. 11, the coil unit 3 is split into an upper coil unit part 29 and a lower coil unit part 30, such that the upper coil unit part 29 may also be attached to the lower coil unit part 30 when the latter is in a hinged position by corresponding attachment device, for example a hook, not shown in FIG. 1 to FIG. 11. Also, not shown are connection devices to connect the upper coil unit part 29 to the lower coil unit part 30 when the lower coil unit part 30 is swung out into the knee position (cf. FIG. 11).

As may also be seen from the figures, the top 24 of the connecting device 2 is formed into a recess 31 enclosing the lower coil unit part 30 largely when in the hinged position, e.g. the folded-up position. Electrical connections from the coil elements (again not shown) to the corresponding connectors of the interface unit 10 are, in this case, provided through the hinges 27.

Figure 7:
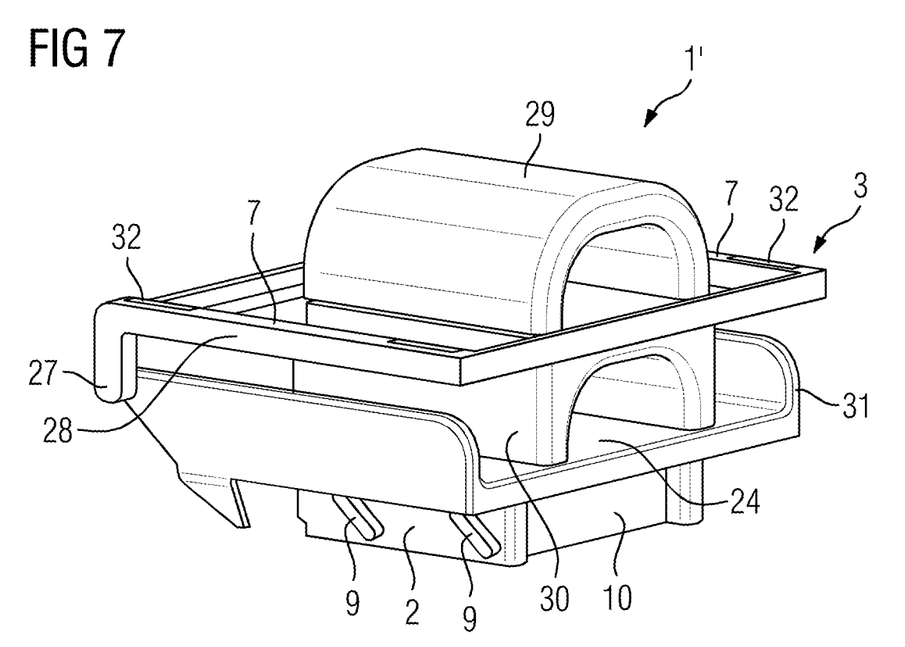
FIG. 7 depicts a perspective view of a local knee coil according to an embodiment.
Figure 8:
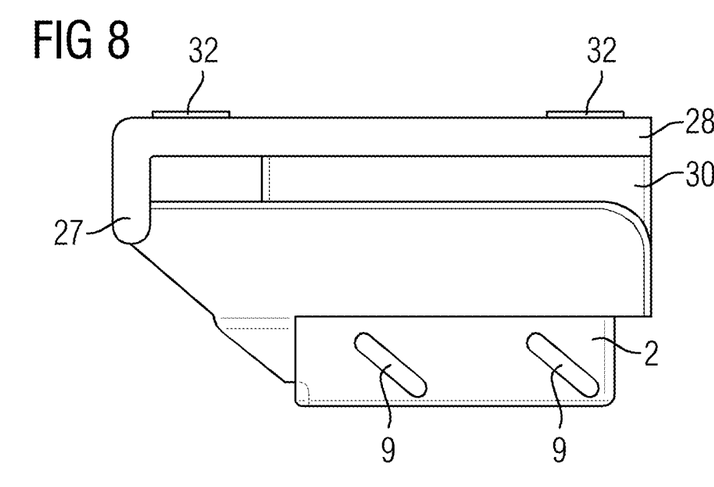
FIG. 8 depicts a side view of the local knee coil of FIG. 7 according to an embodiment.
Figure 9:
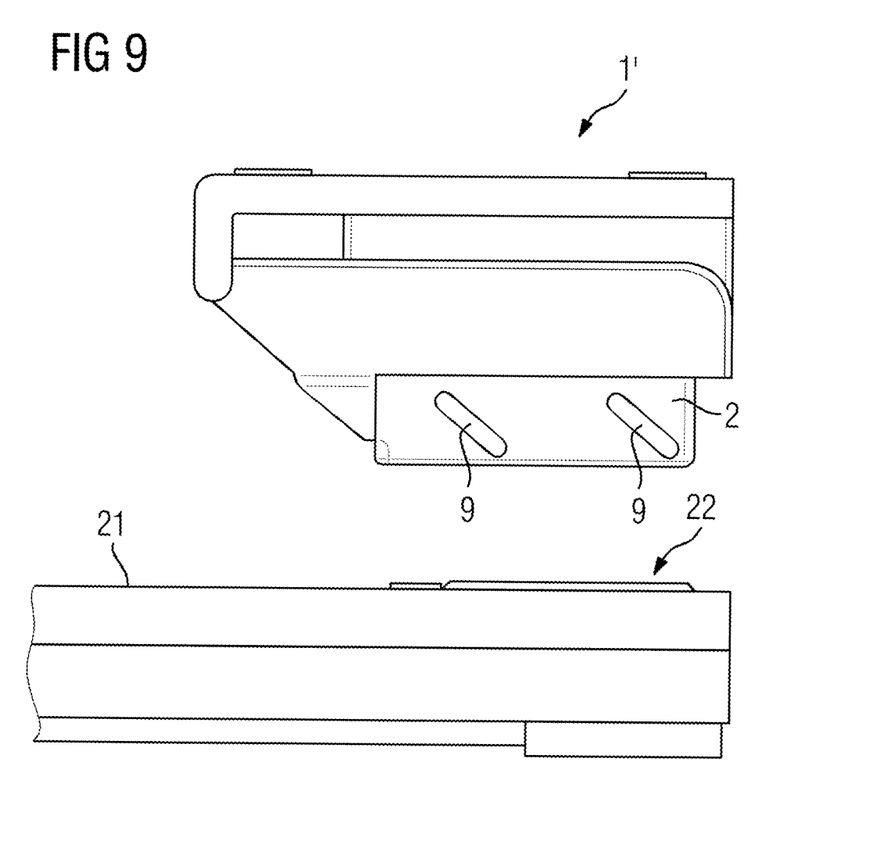
FIG. 9 depicts installing the local knee coil according to an embodiment on a patient table.
Figure 10:
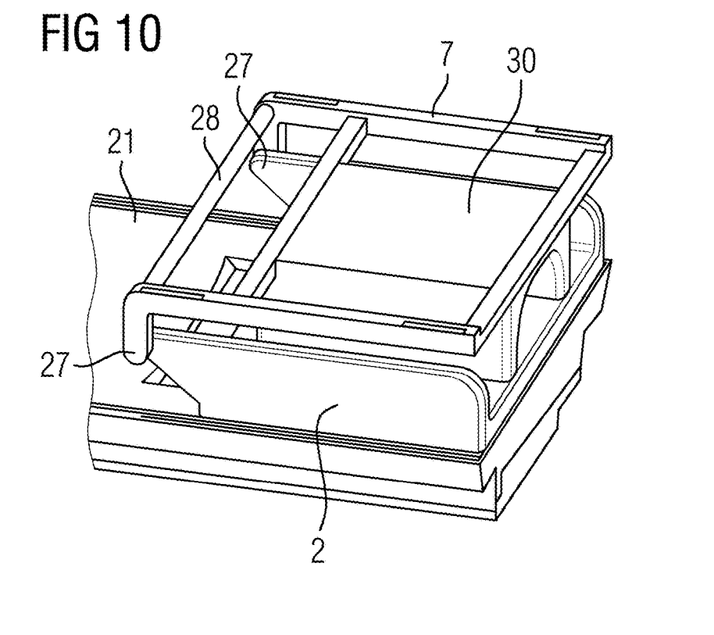
FIG. 10 depicts a perspective view of a local knee coil according to an embodiment installed on a patient table.

To use the local knee coil 1', the upper coil unit part 29 is first removed and, as shown in FIG. 7, the connecting device 2 is fittingly slid into the direct connect socket 22 of the patient table 21, so that the situation shown in FIG. 10 results.

Figure 11:
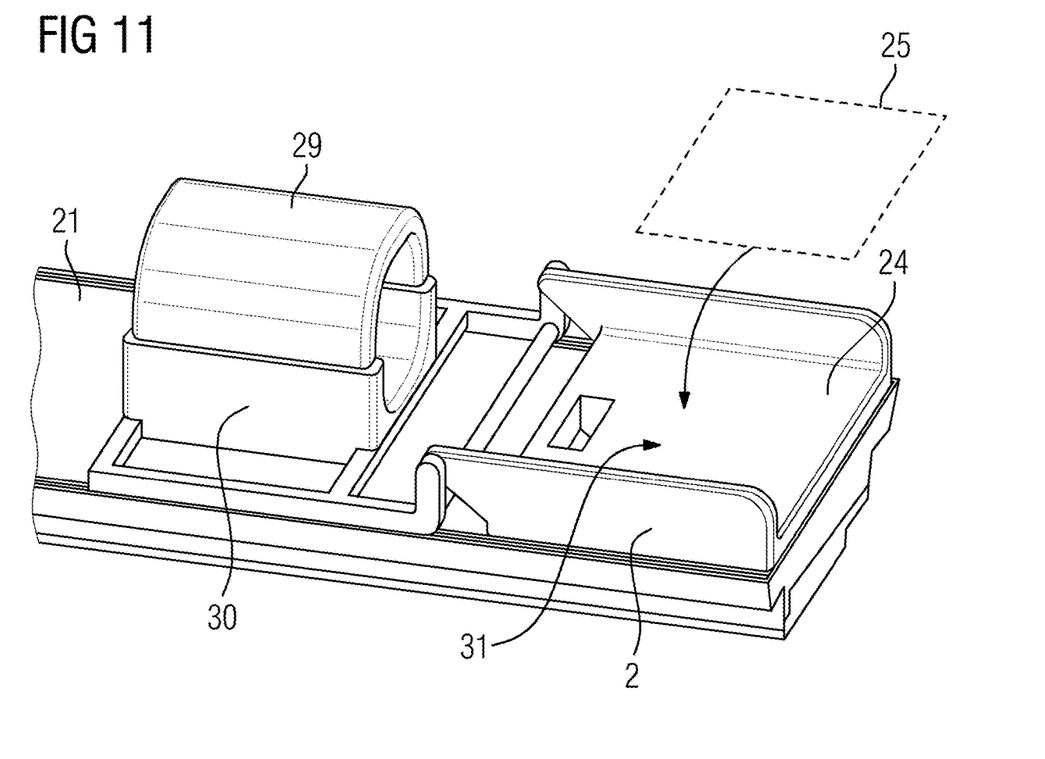
FIG. 11 depicts the local knee coil in a measurement position according to an embodiment.

The lower coil unit part 30 is then swung into the knee position on the patient table 21 by virtue of the hinges 27 as shown in FIG. 11. Thereafter, the upper coil unit part 29 is set on top of the lower coil unit part 30, that may happen after positioning of a knee of a patient inside the lower coil unit part 30.

As may also be seen from FIG. 11, the recess 21 remains empty as soon as the lower coil unit part 30 is swung out, such that it may now be used to place a feet support element 25, for example a cushion, inside this recess to bed the feet and lower legs of the patient comfortably. In an embodiment, the top 24 of the connecting device 2 may also already include a cushion or anatomy recess elements shaped for receiving a part of the anatomy of the patient.

FIGS. 7 to 11 also show guide protrusions 32 along the hinging frame 28 that fit into guide recesses (not shown) in the patient table 21 to further stabilise the coil unit 3 in the knee position. Such guide protrusions may also be provided for the first embodiment.

Figure 12:
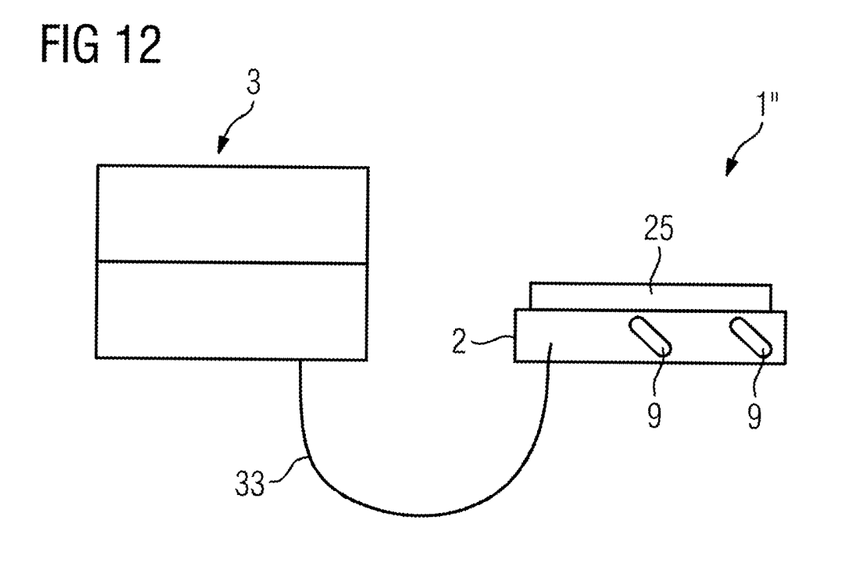
FIG. 12 depicts a third embodiment of a local knee coil.

FIG. 12 depicts an embodiment of a local knee coil 1". In this case, the connecting device 2, still fitting inside the direct connect socket 22 of the patient table 21, is connected to the coil unit 3 using a short cable 33 that is guided laterally away from the space occupied by the patient. The feet support element 25 is attached on top of the connecting device 2.

Figure 13:
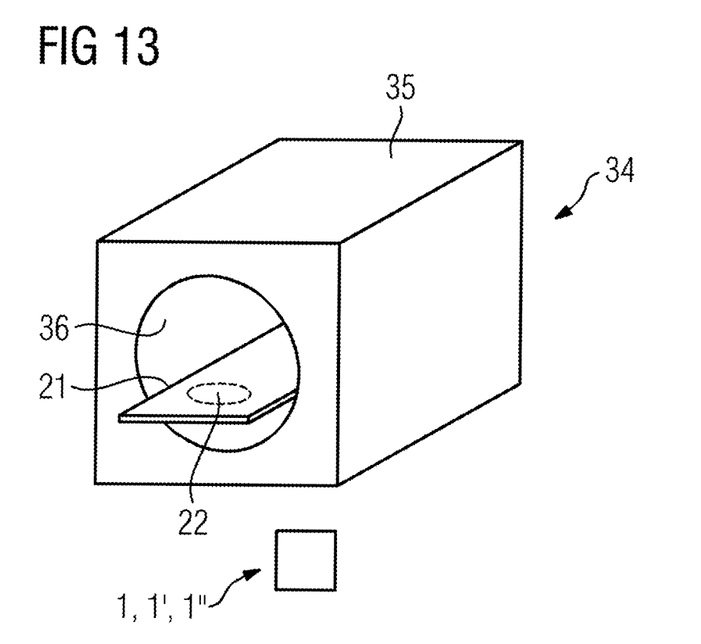
FIG. 13 depicts a magnetic resonance imaging device according to the embodiment.

FIG. 13 depicts a principle drawing of a magnetic resonance imaging device 34. The magnetic resonance imaging device 34 includes a main magnet unit 35 defining a bore 36 into which the patient table 21, including the direct connect socket 22, may be transported. The magnetic resonance imaging device 34 also includes at least one local knee coil 1, 1', 1".

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A local knee coil for a patient table of a magnetic resonance imaging device, the local knee coil comprising:
a connecting device configured to connect to a socket in the patient table, the connecting device comprising at least one connecting device interface unit for multiple channels corresponding to coil elements of the local knee coil, the at least one connecting device interface unit configured to connect to a corresponding socket interface unit of the socket, the connecting device further comprising at least one guiding element to fit the connecting device into the socket that is displaced from a knee position on the patient table, the at least one guiding element configured as a receptacle for the connecting device to form a positive connection and interconnect the at least one connecting device interface unit to the corresponding socket interface unit during the fit;
a coil unit comprising the coil elements configured to send excitation signals, receive magnetic resonance signals, or send excitation signals and receive magnetic resonance signals;
a feet support element for the feet of a patient whose knee extends through the coil unit in the knee position, wherein the feet support element is positioned on a top of the connecting device; and
a displacement device configured to displace at least a part of the coil unit to the knee position on the patient table when the connecting device is connected in the socket, wherein the displacement device comprises a hinge connecting at least part of the coil unit to the connecting device, wherein the at least part of the coil unit is configured to swing out of a folded-up position from atop the connecting device to the knee position.

2. The local knee coil of claim 1, wherein the coil unit is split into an upper coil unit part and a lower coil unit part, wherein the hinge connects the lower coil unit part and the connecting device such that the lower coil unit part swings out from atop the connecting device to the knee position, wherein the upper coil unit part is set atop the lower coil unit part using a connection when the lower coil unit part is swung out.

3. The local knee coil of claim 2, wherein the connecting device comprises a recess for the lower coil unit part, wherein the feet support element is positioned in the recess when the lower coil unit part is swung out.

4. The local knee coil of claim 2, further comprising:
an attachment configured to attach the upper coil unit part to the lower coil unit part or the connecting device when the lower coil unit part and the connecting device are in hinged position.

5. The local knee coil of claim 1, further comprising:
an assembly comprising the coil elements, wherein the assembly is supported by a frame.

6. The local knee coil of claim 5, wherein the frame comprises at least one handle for manually displacing the coil unit, transporting the local knee coil, or displacing and transporting the local knee coil.

7. The local knee coil of claim 1, further comprising:
at least one guiding protrusion interoperable with a corresponding guiding recess of the patient table.

8. The local knee coil of claim 1, wherein the feet support element comprises at least one cushion, at least one anatomy recess element, or at least one cushion and at least one anatomy recess element shaped for receiving a part of the anatomy of the patient.

9. A magnetic resonance imaging device comprising:
a patient table configured with a direct connect socket for a head coil; and
a local knee coil comprising:
a connecting device configured to connect to the direct connect socket in the patient table, the connecting device comprising at least one connecting device interface unit for multiple channels corresponding to coil elements of the local knee coil, the at least one connecting device interface unit connected to a corresponding socket interface unit of the socket, the connecting device further comprising at least one guiding element configured to fit the connecting device into the socket that is displaced from a knee position on the patient table, the at least one guiding element configured as a receptacle for the connecting device to form a positive connection and interconnect the at least one connecting device interface unit to the corresponding socket interface unit during the fit;
a coil unit comprising the coil elements configured to send excitation signals, receive magnetic resonance signals, or send excitation signals and receive magnetic resonance signals;
a feet support element for the feet of a patient whose knee extends through the coil unit in the knee position, wherein the feet support element is positioned on a top of the connecting device; and
a displacement device configured to displace at least a part of the coil unit to the knee position on the patient table when the connecting device is connected in the socket, wherein the displacement device comprises a hinge connecting at least part of the coil unit to the connecting device, wherein the at least part of the coil unit is configured to swing out of a folded-up position from atop the connecting device to the knee position.

10. The magnetic resonance imaging device of claim 9, wherein the local knee coil further comprises:
at least one guiding protrusion interoperable with a corresponding guiding recess of the patient table.

* * * * *